United States Patent [19]

Keil, deceased et al.

[11] 4,414,125

[45] Nov. 8, 1983

[54] ALKALI METAL OR AMINE SALTS OF A MIXTURE OF 2- AND 3-ALKYLADIPIC ACIDS AS CORROSION INHIBITORS

[75] Inventors: Hans S. H. Keil, deceased, late of Marl, Fed. Rep. of Germany, by Inge Keil, legal representative; Helmut Alfs, Marl; Klaus Schulze, Haltern-Lippramsdorf, both of Fed. Rep. of Germany

[73] Assignee: Chemische Werke Huels Aktiengesellschaft, Marl, Fed. Rep. of Germany

[21] Appl. No.: 211,593

[22] Filed: Dec. 1, 1980

[30] Foreign Application Priority Data

Dec. 1, 1979 [DE] Fed. Rep. of Germany ....... 2948503

[51] Int. Cl.$^3$ ...................... C23F 11/14; C23F 11/12; C23F 11/06
[52] U.S. Cl. ........................................ 252/75; 252/76; 252/77; 252/389 R; 252/392; 422/13; 422/16; 422/17
[58] Field of Search ............. 252/8.5 A, 8.5 C, 389 R, 252/392, 76, 77, 75; 422/13, 16, 17

[56] References Cited

U.S. PATENT DOCUMENTS

| | | | |
|---|---|---|---|
| 2,442,672 | 6/1948 | von Fuchs et al. | 252/56 |
| 2,726,215 | 12/1955 | Jones | 252/389 R |
| 2,947,699 | 8/1960 | Wasson et al. | 252/389 X |
| 2,971,915 | 2/1961 | Borsoff et al. | 252/56 |
| 3,087,936 | 4/1963 | Le Seur . | |
| 3,238,136 | 3/1966 | Willard et al. | 252/389 X |
| 3,696,048 | 10/1972 | Hausler et al. | 252/392 |
| 3,981,780 | 9/1976 | Scherrer et al. | 252/392 X |
| 4,210,549 | 7/1980 | Hirozawa et al. | 252/389 X |
| 4,250,042 | 2/1981 | Higgins | 252/8.5 |

FOREIGN PATENT DOCUMENTS

| | | |
|---|---|---|
| 53-79738 | 7/1978 | Japan . |
| 984409 | 2/1965 | United Kingdom . |
| 995708 | 6/1965 | United Kingdom . |

*Primary Examiner*—Herbert B. Guynn
*Attorney, Agent, or Firm*—Millen & White

[57] ABSTRACT

A corrosion inhibited composition comprises an aqueous drilling, cutting, or polishing agent, an aqueous hydraulic fluid or an aqueous antifreeze compound; and an alkali metal salt, or an aliphatic amine salt of a mixture of 2- and 3-$C_{6-12}$-alkyladipic acids, the amount of this acid component being effective as a corrosion inhibitor.

11 Claims, No Drawings

ALKALI METAL OR AMINE SALTS OF A MIXTURE OF 2- AND 3-ALKYLADIPIC ACIDS AS CORROSION INHIBITORS

BACKGROUND OF THE INVENTION

It is known from U.S. Pat. No. 2,726,215 to use alkali metal salts of azelaic or sebacic acids as corrosion inhibitors for aqueous solutions. British patent specification No. 995 708 describes the use of alkanolamine salts of azelaic and sebacic acids in aqueous drilling and cutting fluids based on polyoxyalkylenes. However, the corrosion-protective properties of salts of azelaic and sebacic acids are not optimal and leave room for improvement, as can be seen from Tables 1 and 3.

It is the state of the art, per the disclosure of U.S. Pat. No. 2,442,672, to add alkylsuccinic acid to hydrocarbon oils as a rust inhibitor, while U.S. Pat. No. 2,971,915 describes the addition of alkyladipic acids having a short side chain, such as methyladipic acid. Alkylsuccinic acids have the disadvantage in aqueous media of forming insoluble alkaline earth metal salts with the hardness-causing compounds of water. These thus precipitate out. On the other hand, short-chain alkyladipic acids, even in the form of their amine salts, still provide inadequate rust protection (cf. Table 1).

It is further known from British patent specification No. 984 409 and U.S. Pat. No. 3,087,936 to add amine salts of substituted succinic acids to lubricating oils for purification purposes and/or for sludge prevention. These amine salts have substituents having a C number of ≧30. On the one hand, these references do not teach how to prevent metal corrosion in aqueous systems; on the other hand, the respective amine salts involved do not possess sufficient water solubility for such purposes anyway due to the high C number of their substituents.

Under practical conditions, for economic reasons, it is still customary to utilize aqueous fluids containing alkanolamines and sodium nitrite for simple metal machining, for example for grinding and polishing. However, it has been found that carcinogenic nitrosamines are thus formed from nitrite and alkanolamines. In addition, two other commercial products are utilized in a large number of cases as rust-inhibiting additives for metal-machining agents in aqueous systems. Commercial product A is the triethanolamine salt of an acrylsulfonamidoalkylenecarboxylic acid (German Patent No. 1,298,672); commercial product B is a mixture of fatty acid diethanolamide and fatty acid diethanolamine salts. Both commercial products, as seen from Table 1, achieve a rust-protective effect which, especially in the low concentration range, still needs improvement.

SUMMARY OF THE INVENTION

Accordingly, it is an object of this invention to provide new corrosion inhibitors which are highly effective and lack the aforementioned disadvantages.

Upon further study of the specification and appended claims, further objects and advantages of this invention will become apparent to those skilled in the art.

These objects have been achieved and the disadvantages of the prior art avoided by providing alkali metal or amine salts of a mixture of 2- and 3-alkyladipic acids, the alkyl residues of which are branched or unbranched and contain 6–12 carbon atoms.

These can be advantageously employed as corrosion inhibitors for drilling, cutting, polishing and grinding agents, hydraulic fluids and antifreeze fluids, all containing water as the primary component.

DETAILED DESCRIPTION

These alkali or amine salts are normally utilized in drilling, cutting, grinding etc. agents in concentrations of 0.5–3%, preferably 1.0–2.5% by weight, based on the total weight of the entire, drilling, cutting or grinding agent. In hydraulic fluids, these alkali or amine salts are normally employed in concentrations of 1–5% by weight, preferably 2.0–3.5%, based on the total weight of the entire hydraulic fluid. In antifreeze compounds, the alkali or amine salts are normally used in concentrations of 0.6–1.7% by weight, preferably 0.9–1.3%, based on the total weight of the entire antifreeze composition.

If the alkali metal or amine salts of this invention are used in conjunction with other conventional corrosion inhibitors, e.g., in antifreeze compositions, a concentration of 0.6–1.0% by weight, based on the entire antifreeze concentrate, is generally adequate. In general, for any composition, other conventional inhibitors can be employed in addition to the inhibitors of this invention.

The mixtures of 2- and 3-alkyladipic acids, the alkali or amine salts of which are to be used in accordance with this invention, can be prepared by conventional alkylation of phenol with an olefin of 6–12 carbon atoms in the presence of an acid, a Lewis acid or an acidic ion exchanger; catalytic hydrogenation of the thus-obtained alkyl phenol to the corresponding alkylcyclohexanol, in a manner also known per se; and subsequent oxidation with nitric acid, as is likewise conventional.

The alkyl phenol mixtures suitable as starting materials for preparing the mixtures of 2- and 3-alkyladipic acids of this invention can be produced by chemically adding olefins, such as hexene, octene, diisobutylene, tripropylene, tetrapropylene, or dodecene, to phenol. From diisobutylene and phenol, there is obtained a mixture of predominantly p-isooctylphenol and a small amount of o-isooctylphenol; from tripropylene and phenol, a mixture is produced of primarily p-isononylphenol and a small amount of o-isononylphenol. When chemically adding unbranched olefins to phenol, in contrast to the above, mixtures of the o- and p-isomers are obtained wherein the o-isomer is predominant. An especially advantageous mode of operation for the preparation of the alkyl phenols is described in J. Klein, H. Widdecke, "Chem.-Ing.-Techn." [Chemistry Engineering Technology] 51: 6, 560 (1979), whose disclosure is incorporated by reference herein.

The alkylated phenols can be conventionally hydrogenated, e.g., using the procedures of DOS [German Unexamined Laid-Open-Application] 23 34 928. whose disclosure is incorporated by reference herein.

An especially advantageous method of oxidizing the thus obtained alkylcyclohexanols with nitric acid is described in German Patent No. 1,643,854, whose disclosures are incorporated by reference herein.

The use of the term alkyladipic acid(s) throughout the following description is meant to include mixtures of 2- and 3-alkyladipic acids such as those obtained, for example, by the mentioned preparative process, i.e., by chemical addition of olefins to phenol, hydrogenation of the alkyl phenols to alkylcyclohexanols, and subsequent oxidation, for example, with nitric acid.

In general, the adipic acid chains predominantly have only one alkyl substituent. Di-substituted acids are used only in minor contents. As can be seen, the percentage content of each of the 2- and 3-alkyl adipic acid salts in a given mixture of salts is not critical and will vary predominantly with the details of the preparation of the acids.

Suitable alkyladipic acids, the alkali or amine salts of which can be used in accordance with this invention, include, for example: n-hexyladipic acid, n-octyladipic acid, n-decyladipic acid, n-dodecyladipic acid, isooctyladipic acid, isononyladipic acid, isododecyladipic acid.

Suitable for the production of the amine salts of the suitable alkyladipic acids are water-soluble, primary, secondary or tertiary, aliphatic amines, diamines, alkanolamines, as well as polyalkylene polyamines. In general, each alkyl moiety has 1–6 carbon atoms, the number not being critical.

Examples include methylamine, ethylamine, n-propylamine, n-butylamine, n-pentylamine, dimethylamine, diethylamine, di-n-propylamine, di-n-butylamine, isopropylamine, isobutylamine, isopentylamine, diisopropylamine, diisobutylamine, etc.; alkanolamines, such as ethanolamine, diethanolamine, triethanolamine, isopropanolamine, diisopropanolamine, triisopropanolamine, etc.; alkyl alkanolamines, such as methyldiethanolamine, ethyldiethanolamine, propyldiethanolamine, butyldiethanolamine, pentyldiethanolamine, hexyldiethanolamine, dimethylethanolamine, diethylethanolamine, dipropylethanolamine, dibutylethanolamine, dipentylethanolamine, etc.; diamines, such as N-ethylpropanediamine, N-diethylpropanediamine, N-propylpropanediamine, morpholylpropylamine, etc.; polyalkylene polyamines, such as ethylenediamine, diethylenetriamine, triethylenetetramine, tetraethylenepentamine, as well as the equivalent ethoxylation products of any of these amines with up to 10 oxyethyl groups.

Preferably utilized as the amine salts are triethanol- and triisopropanolamine salts of isooctyl- and isononyladipic acids. However, likewise suitable are the triethanolamine and triisopropanolamine salts of n-hexyladipic acid, of n-octyladipic acid, of n-decyladipic acid, of n-dodecyladipic acid, and of isododecyladipic acid.

The amine salts of this invention are suitably prepared by combining the amine with the alkyladipic acid and heating the mixture to 60°–90° C. under agitation for a time period of 5–15 minutes. Approximately stoichiometric amounts are generally employed, i.e., about a 2:1 or slightly larger molar ratio of amine to acid.

Suitable alkali metal salts of the alkyladipic acids to be utilized in accordance with this invention include Na and K salts. As for the amine salts, these salts are also difunctional, i.e. disalts.

Suitable media wherein the salts of the alkyladipic acids described herein are particularly useful as corrosion inhibitors include, for example, the following conventional agents:

(1) Drilling, cutting, and polishing agents, consisting of
(a)
   (i) 90–98% by weight of water, and
   (ii) 10–2% by weight of glycols, polyglycols, polyglycol ethers, or water-soluble polymers of ethylene oxide and propylene oxide, or homo- or copolymers of acrylic acid, methacrylic acid or maleic acid anhydride and olefins, and
   (iii) subordinate amounts of nonferrous metal inhibitors; or
(b)
   (i) 90–98% by weight of water,
   (ii) 7–2% by weight of mineral oil, and
   (iii) 3–1% by weight of emulsifiers.

These agents are used as emulsions.

(2) Hydraulic fluids, consisting of:
(a)
   (i) 40–50% by weight of water
   (ii) 20–25% by weight of a thickener, for example, a mixed adduct of ethylene oxide and propylene oxide,
   (iii) 35–20% by weight of a glycol, and
   (iv) 10–5% by weight of customary additives, such as inhibitors, alkanolamines, vapor-phase corrosion-protection agents, etc., or
(b) oil-in-water emulsions with customary additives.

(3) Antifreeze compounds, consisting of:
25–40% by weight of inhibited glycol, remainder up to 100% by weight of water.

For example, a corrosion inhibited composition of this invention comprises:
(a) water
(b) a glycol; a polyglycol; a polyglycol ether; a water soluble polymer of ethylene oxide and propylene oxide; a homo- or copolymer of acrylic acid, methacrylic acid or maleic acid or anhydride, and an olefin; a mineral oil; an emulsifier; or a thickener for aqueous compositions; and
(c) an alkali metal salt or an aliphatic amine salt of a mixture of 2- and 3-$C_{6-12}$-alkyladipic acids, the amount of this acid component being effective as a corrosion inhibitor.

Suitable conventional inhibitor components for co-use include, for example: Na benzoate, borax, Na nitrite, Na nitrate, Na metal silicate, benzotriazole, ε-aminopentylimidazoline, sodium carbonate etc. Furthermore, conventional defrothers can be utilized.

The finished formulations containing the inhibitors of this invention should have a pH of 7.0 to 9.0, preferably 7.2 to 8.0.

The alkali metal salts of alkyladipic acids per this invention can be utilized, especially, in brake fluids and in antifreeze compounds.

In the brake fluids of the prior art, e.g. the conventionally employed borax can be substituted, for example, by a potassium salt of alkyladipic acids, whereby at least equally high corrosion protection effects and improved frictional wear protection properties are achieved.

In antifreeze agents, these alkali metal salts of alkyladipic acids can, e.g., replace the sodium benzoate presently used in formulations, whereby improved corrosion-protection values are obtained.

Customary corrosion inhibitors which can be used together with the salts of alkyladipic acids to be employed in this invention include, for example: Na nitrite, borax, Na nitrite, Na metal silicate, and nonferrous metal inhibitors, such as, for example, ε-aminopentylimidazoline, benzotriazole, etc.

Without further elaboration, it is believed that one skilled in the art can, using the preceding description, utilize the present invention to its fullest extent, the following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

The following examples also prove the advance in the art attained by this invention.

EXAMPLE 1

Preparation of Isooctyladipic Acid (This preparation example applies analogously to an exemplary preparation of all alkyladipic acids which can be utilized according to this invention.)

340 kg of diisobutene and 570 kg of phenol are mixed, preheated to about 70° C., and pumped through two series-connected reactors, each filled with 120 kg of catalyst (see the detailed description in German Patent No. 2,346,273, whose disclosure is incorporated by reference herein).

The crude alkylate contained about 63% octyl phenol.

After working up the mixture by distillation, an octyl phenol is obtained having the following composition:

| | |
|---|---|
| Phenol content | ≦0.2% by weight |
| Octylphenol content | ≧95% by weight |
| Remainder (primarily dialkyl phenol) | ≦5% by weight |

The octyl phenol consists of about 98% para isomers and about 2% ortho isomers.

Hydrogenation is conducted under standard conditions at 160° C. under a pressure of 1 atmosphere in the presence of Pd on $Al_2O_3$ (Engelhardt catalyst).

The octylcyclohexanol obtained by distillation has a high degree of purity and has the following properties:

| | |
|---|---|
| Color APHA | ~5 |
| $D_4^{20}$ | 0.9254 |
| Phenol | <0.01% |
| OH Number | 261.4 |
| b.p. 27 mbar | 161.5–167.5 |

The oxidation is conducted in an apparatus which is a 4-liter agitated flask equipped with a dropping funnel, temperature measuring device and cooling bath. Within 3 hours, 424 g of octylcyclohexanol is added dropwise at 60°–65° C. to 1,300 g of nitric acid "40" Be. The mixture is then agitated for 1 hour at 60° C. The content of the flask is allowed to stand overnight and then is vacuum-filtered and washed free of $HNO_3$ with ice water.

The dried acid had an acid number of 421.

Tables 1, 2, and 3 compare conventional corrosion inhibitors based on mono- and dicarboxylic acids with respect to their corrosion-protection action. In the indicated formulations, the total amount of inhibitor, i.e. acid and amines, was approximately the same in each case, and the amine-acid ratio was adjusted so that the pH of a 5% aqueous solution was always approximately 7.5.

Testing for corrosion-protective effect was conducted in accordance with DIN [German Industrial Standard] 51 360, Part 1 and Part 2.

In the modus operandi of Part 1, steel milling chips are applied to a cleaned test plate of cast iron and wetted with the water-mixed cooling lubricant. After a residence time of 24 hours in the testing chamber at room temperature and an atmospheric relative humidity of 50–60%, the steel chips and the oil-free surface of the test plate are examined for corrosion.

According to the mode of operation of Part 2, cast-iron chips GG 30 are wetted on a round filter with the freshly prepared, aqueous corrosion-protection solution, left for 2 hours in a sealed Petri dish at room temperature, and then the round filter is visually inspected for signs of corrosion as follows:

| Evaluation of the Degree of Corrosion According to DIN 51 360 Part 1 in Tables 1–3 |
|---|
| 0 = no corrosion |
| 1 = traces of corrosion |
| 2 = slight corrosion (corroded area 10%) |
| 3 = moderate corrosion (corroded area 10–25%) |
| 4 = intensified corrosion (corroded area 25–50%) |
| 5 = strong corrosion (corroded area 50–75%) |
| 6 = very strong corrosion (corroded area above 75%) |
| Degrees of Corrosion of the Corrosion Manifestations on the Round Filter According to DIN 51 360, Part 2 |
| 0 = no corrosion, surface of round filter unchanged |
| 1 = traces of corrosion, at most 3 rust spots |
| 2 = slight corrosion, no more than 1% of area discolored |
| 3 = moderate corrosion, up to 5% of area discolored |
| 4 = strong corrosion, more than 5% of area discolored by rust |

TABLE 1

| | State of the Art | | | | | | | |
|---|---|---|---|---|---|---|---|---|
| | 1 | 2 | 3 | 4 | 5 | 6 | 7 | 8 |
| Acid used | Benzoic acid | 4-tert.-Butyl-benzoic acid | 4-Dode-cyl-benzoic acid | Azelaic acid | Sebacic acid | Adipic acid | 2,4,4'-Tri-methyl-adipic acid | 2-tert.-Butyl-adipic acid |
| Purity in % by Weight | 98 | about 95 | about 92 | about 95 | about 98 | 98 | 94 | 92 |
| Molecular Weight | 122 | 180 | 290 | 188 | 202 | 146 | 188 | 202 |
| Amount in % by Weight | 23 | 27 | 32 | 18 | 19 | 15 | 18 | 19 |
| Triisopropanol-amine Amount in % by Weight | 46 | 38 | 31 | 46 | 46 | 50 | 50 | 48 |
| 1,2-Propylene Glycol Amount in % by Weight | 14 | 14 | 14 | 14 | 14 | 12 | 12 | 14 |
| Distilled Water Amount in % by Weight | 17 | 21 | 23 | 22 | 21 | 23 | 20 | 19 |
| pH Value of a 5% Aqueous | 7.45 | 7.4 | 7.5 | 7.45 | 7.4 | 7.55 | 7.4 | 7.45 |

TABLE 1-continued

| | State of the Art | | | | | | | | | | | | | | | | | | | | | | | |
|---|---|---|---|---|---|---|---|---|---|---|---|---|---|---|---|---|---|---|---|---|---|---|---|---|
| | 1 | | | 2 | | | 3 | | | 4 | | | 5 | | | 6 | | | 7 | | | 8 | | |
| Solution % by Weight in Drinking Water 8° dGH | 0.5 | 1.0 | 2.0 | 0.5 | 1.0 | 2.0 | 0.5 | 1.0 | 2.0 | 0.5 | 1.0 | 2.0 | 0.5 | 1.0 | 2.0 | 0.5 | 1.0 | 2.0 | 0.5 | 1.0 | 2.0 | 0.5 | 1.0 | 2.0 |
| Corrosion Test According to DIN 51 360 Part 1 | 6 | 5 | 3 | 5 | 4 | 2 | 6 | 4 | 1 | 4–5 | 3 | 0 | 5 | 2–3 | 1 | 6 | 6 | 5 | 6 | 6 | 6 | 5 | 4 | 3 |
| Corrosion Test According to DIN 51 360 Part 2 (Chip Test) | 4 | 4 | 3–4 | 4 | 4 | 3 | 4 | 2 | 1–2 | 4 | 2–3 | 0–1 | 4 | 3 | 1 | 4 | 4 | 4 | 4 | 4 | 4 | 4 | 4 | 3–4 |

Evaluation of the Degree of Corrosion According to DIN 51 360, Part 1 in Tables 1-3
0 = no corrosion
1 = traces of corrosion
2 = slight corrosion (corroded area 10%)
3 = moderate corrosion (corroded area 10-25%)
4 = intensified corrosion (corroded area 25-50%)
5 = strong corrosion (corroded area 50-75%)
6 = very strong corrosion (corroded area above 75%)
Degrees of Corrosion of the Corrosion Manifestations on the Round Filter According to DIN 51 360, Part 2
0 = no corrosion, surface of round filter unchanged
1 = traces of corrosion, at most 3 rust spots
2 = slight corrosion, no more than 1% of area discolored
3 = moderate corrosion, up to 5% of area discolored
4 = strong corrosion, more than 5% of area discolored by rust

TABLE 2

| | According to Invention | | | | State of the Art | | |
|---|---|---|---|---|---|---|---|
| | 9 | 10 | 11 | 12 | 13 | 14 | 15 |
| Acid or Inhibitor Used | Hexyl-adipic acid | Isooctyl-adipic acid | Isononyl-adipic acid | Dodecyl-adipic acid | Oleic acid | Commercial product A (1) | Commercial product B (2) |
| Purity in Weight Percent | about 93 | about 94 | about 92 | about 93 | about 96 | — | — |
| Molecular Weight | 230 | 258 | 272 | 300 | 282 | — | — |
| Amount in Weight Percent | 25 | 24 | 25 | 27 | 26 | 100 | 70 |
| Triisopropanolamine Amount in weight percent | 49 | 46 | 45 | 44 | 46 | — | — |
| 1,2-Propylene Glycol Amount in Weight Percent | 12 | 14 | 14 | 14 | 14 | — | 14 |
| Distilled Water Amount in Weight Percent | 15 | 16 | 16 | 15 | 14 | — | 16 |
| pH Value of a 5% Aqueous Solution | 7.55 | 7.55 | 7.6 | 7.6 | 7.65 | 8.35 | 10.3 |
| Weight Percent in Drinking Water 8° dGH | 0.5 / 1.0 / 2.0 | 0.5 / 1.0 / 2.0 | 0.5 / 1.0 / 2.0 | 0.5 / 1.0 / 2.0 | 0.5 / 1.0 / 2.0 | 0.5 / 1.0 / 2.0 | 0.5 / 1.5 / 2.5 |
| Corrosion Test According to DIN 51 360 Part 1 | 3 / 0 / 0 | 2–3 / 0 / 0 | 3 / 0–1 / 0 | 3 / 0 / 0 | 6 / 4 / 2 | 4 / 2 / 0 | 5 / 3–4 / 1–2 |
| Corrosion Test According to DIN 51 360 Part 2 (Chip Test) | 3–4 / 1–2 / 0 | 2–3 / 1 / 0 | 3–4 / 1 / 0 | 3–4 / 2 / 0 | 4 / 4 / 3–4 | 4 / 3–4 / 0–1 | 4 / 3–4 / 2–3 |

(1) Salt of an arylsulfonamidoalkylenecarboxylic acid with triethanolamine according to German Patent 1,298,672.
(2) Mixture of fatty acid diethanolamide with fatty acid diethanolamine salts.
Evaluation of the Degree of Corrosion According to DIN 51 360, Part 1 in Tables 1-3
0 = no corrosion
1 = traces of corrosion
2 = slight corrosion (corroded area 10%)
3 = moderate corrosion (corrodes area 10-25%)
4 = intensified corrosion (corroded area 25-50%)
5 = strong corrosion (corroded area 50-75%)
6 = very strong corrosion (corroded area above 75%)
Degrees of Corrosion of the Corrosion Manifestations on the Round Filter According to DIN 51 360, Part 2
0 = no corrosion, surface of round filter unchanged
1 = traces of corrosion, at most 3 rust spots
2 = slight corrosion, no more than 1% of area discolored
3 = moderate corrosion, up to 5% of area discolored
4 = strong corrosion, more than 5% of area discolored by rust

TABLE 3

|  | 16 | 17 | 18 | 19 | 20 | 21 | 22 | 23 |
|---|---|---|---|---|---|---|---|---|
| Acid Utilized | Isooctyl-adipic acid | Isooctyl-adipic acid | Isooctyl-adipic acid | Isononyl-adipic acid | Isononyl-adipic acid | Isodecyl-adipic acid | Azelaic acid | Sebacic acid |
| Molecular Weight | 258 | 258 | 258 | 272 | 272 | 300 | 188 | 202 |
| Alkali | Sodium | Potassium | Potassium | Sodium | Potassium | Sodium | Sodium | Sodium |
| Alkali Content in Moles | 2.1:1 | 2.1:1 | 2:1 | 2:1 | 2.1:1 | 2:1 | 2.1:1 | 2:1 |
| 1,2-Propylene Glycol, Amount in Weight Percent | — | — | 54 | — | — | — | — | — |
| Water, Amount in Weight Percent | — | — | 6 | — | — | — | — | — |
| pH Value of a 5% Aqueous Solution | 7.3 | 8.0 | 7.8 | 7.6 | 7.8 | 8.0 | 7.9 | 7.9 |
| Weight Percent in Drinking Water 8° dGH | 0.5 1.0 2.0 | 0.5 1.0 2.0 | 0.5 1.0 2.0 | 0.5 1.0 2.0 | 0.5 1.0 2.0 | 0.5 1.0 2.0 | 0.5 1.0 2.0 | 0.5 1.0 2.0 |
| Corrosion Test According to DIN 51 360 Part 1 | 2 0 0 | 1 0 0 | 2-3 1 0 | 1-2 0 0 | 1 0 0 | 1-2 0 0 | 2 1 0 | 3 1-2 0 |
| Corrosion Test According to DIN 51 360 Part 2 (Chip Test) | 2 0 0 | 1-2 0-1 0 | 2 1 0 | 0-1 1 0 | 1 0 0 | 1 0 0 | 3 1-2 0 | 4 2 0 |

The results show that benzoic acid, its alkylated derivatives, oleic acids, adipic acid, and/or short-chain-alkylated adipic acids in a concentration range from 0.5 to 2% by weight, display no rust-protection effect on iron or only a low rust-protection effect. No comparison tests were conducted with salts of alkylsuccinic acids, since these acids formed precipitates with the hardness-causing compounds contained in water having a hardness of 8° dGH.

Alkyladipic acids starting with a chain length of 6 carbon atoms, and starting with concentrations of 1% showed very good corrosion protection. In minor concentrations, this rust-proofing effect is markedly better as compared to the simultaneously tested azelaic and sebacic acids. Also in the case of the alkali metal salts of these acids, which were used as pure, dry salts for preparing the solutions, the alkali metal salts of alkyladipic acids, in low concentrations of up to 1% by weight, likewise show a markedly improved corrosion-protective effect as compared with the solution of the alkali metal salts of azelaic and sebacic acids.

In a comparison with commercial corrosion-protection agents, i.e., commercial product A (a triethanolamine salt of alkylsulfonamidoalkylene carboxylic acid) and commercial product B (a mixture of fatty acid diethanolamide and fatty acid ethanolamine salts), the additives of this invention displayed a clearly better rustproofing effect. As compared to commercial product A, the corrosion-preventive agents of this invention were especially superior in low concentration ranges of below 2% by weight.

EXAMPLE 2

An emulsifiable mineral oil was prepared according to conventional procedures from a spindle oil raffinate (20 mm²/sec at 50° C.) using a sodium petroleum sulfonate (molecular weight 450) and an oleic acid triethanolamine salt. The aqueous emulsion showed just barely sufficient corrosion protection in a concentration of 5 vol % according to DIN 51 360, Part 2. After the addition of 4% by weight of a mixture according to Example 10, Table 2, or 4% by weight of a 40% solution of the potassium salt of isononyladipic acid in butyl diglycol/water, to the emulsifiable mineral oil concentrate, good corrosion protection could still be achieved with a 2% emulsion. For the same rust-preventive effect, the addition of 8% by weight of commercial product B or 7% by weight of the mineral-oil-containing standard product, commercial product A, was necessary. This proves the surprising effect of the corrosion inhibitors of this invention.

Analogous findings regarding corrosion protection are observed with the addition of the potassium salt of alkyladipic acids when using, instead of the emulsifier based on a sodium petroleum sulfonate, suitable nonionic emulsifiers, for example of the type of ethoxylated nonyl phenol or an oleic acid oxyethylate.

EXAMPLE 3

To produce inhibited glycols for use as antifreeze agents for automobile cooling systems, the inhibitor mixtures set forth below were tested according to ASTM D 1384-70. The data in Table 4 are given in terms of percent by weight:

| Corrosion Characteristic According to ASTM D 1384-70 Weight Loss in g/m² | | | | | | | |
|---|---|---|---|---|---|---|---|
|  | 1 | 2 | 3 | 4 | 5 | 6 | 7 |
| Copper | 26.1 | 5.7 | 3.8 | 2.9 | 0.7 | 0.9 | 0.7 |
| Solder on brass | 24.9 | 0.2 | 1.9 | 0.7 | 0.9 | 0.0 | 0.1 |
| Brass | 76.0 | 2.8 | 2.4 | 3.1 | 1.5 | 1.6 | 0.9 |
| Steel | 186.8 | 0.2 | 0.5 | 0.3 | 0.8 | 0.0 | 0.0 |
| Cast iron | 34.9 | 0.0 | 0.0 | 0.1 | 0.4 | 0.0 | 0.0 |
| Aluminum | 4.8 | 1.7 | 3.5 | 5.8 | 1.5 | 0.9 | 1.2 |

TABLE 4

|  | 1 | 2 | 3 | 4 | 5 | 6 | 7 |
|---|---|---|---|---|---|---|---|
| Sodium benzoate | 5.00 | — | 4.00 | — | 2.50 | — | — |

TABLE 4-continued

|  | 1 | 2 | 3 | 4 | 5 | 6 | 7 |
|---|---|---|---|---|---|---|---|
| Sodium salt of 2-isooctyladipic acid | — | 5.00 | — | 4.00 | — | 2.50 | 2.50 |
| Borax % 10% water | — | — | 1.00 | — | 1.40 | 1.40 | 1.40 |
| Sodium nitrite | — | — | 0.45 | 0.40 | 0.25 | 0.25 | 0.25 |
| Sodium nitrate | — | — | — | — | 0.15 | 0.15 | 0.15 |
| Sodium metasilicate pentahydrate | — | — | — | — | 0.10 | 0.10 | 0.10 |
| ε-Aminopentylimidazoline | — | — | — | — | 0.10 | 0.10 | 0.10 |
| Water | — | — | — | — | 1.00 | 1.00 | 1.00 |
| Defrother on silicone base | 0.02 | 0.02 | 0.02 | 0.02 | 0.02 | 0.02 | 0.02 |
| Ethylene glycol | 94.98 | 94.98 | 94.03 | 95.58 | 94.48 | 94.48 | — |
| 1,2-Propylene glycol | — | — | — | — | — | — | 94.48 |
| Reserve alkalinity | 1.75 | 10.20 | 8.40 | 9.70 | 14.10 | 15.50 | 15.60 |

The results show that sodium benzoate in existing formulations can be replaced by an alkali metal salt of an alkyladipic acid. The sodium salt of isooctyladipic acid yields in every case considerably better corrosion protection values than sodium benzoate or borax do when used as the sole inhibitor. The sodium salt of isooctyladipic acid can also be used or the inhibition of 1,2-propylene glycol in combination with other inhibitors, for example those of German Patent Nos. 1,154,976 or 2,149,138. Sodium benzoate is insoluble in this glycol. (The above formulations are not optimized with respect to the use of alkali metal salts of alkyladipic acids, i.e. the addition of other, known inhibitors is not listed.)

EXAMPLE 4

Internationally, brake fluids are tested for corrosion according to the specification SAE J 1703 f. In this testing method, test strips of the metals of tin-plated iron, steel, aluminum, cast iron, brass, and copper are screwed together after an appropriate cleaning in the indicated sequence. They are overlaid with the liquid in a glass beaker with perforated metal lid. The brake fluid to be tested is previously combined with 5% by weight of distilled water. Testing is carried out for 120 hours at a temperature of 100° C.

A brake fluid having a boiling point of 250° C. was composed of the components: mixed adduct of 1.5 mole of propylene oxide to 1 mole of diethylene glycol monoethyl ether, ethyl triglycol, butyl triglycol, diethylene glycol, and polypropylene glycol 620. The inhibitor used was an alkali borate-glycol complex according to DAS Nos. 1,295,124 or DOS 1,643,287, or the potassium salt of isooctyladipic acids in approximately equal contents. The alkali borate complex ester in ethylene glycol was added in a quantity of 3% by weight; the potassium salt was added in an amount of 2.5% by weight. The potassium salt showed a good solubility in the thus-prepared brake fluid, even at low temperatures.

The hydraulic fluids per se had a boiling point according to ASTM D 1120 of 252° C., and a viscosity according to ASTM D 445 of 1.7 mm²/sec at 100° C. and 1,252 mm²/sec at −40°0 C. After adding 3% by weight of an inhibitor concentrate according to Example 2 of DOS 1,643,287 and/or 2.5% by weight of the dry potassium salt of isooctyladipic acids (2.1 mole of potassium hydroxide (22.4 g 50% aqueous potassium hydroxide solution) and 1 mole of isooctyladipic acids (25.8 g of isooctyladipic acids)), the oxidation test of SAE J 1703 f, section 4, 10 was likewise satisfied. In the corrosion test according to SAE J 1703 f, item 4, 5, the following results were achieved (weight losses in mg/cm²):

|  | Limit According to DOT 3 | With Inhibitor According to 1,643,287, Example 2 | According to Invention |
|---|---|---|---|
| Tin-plated iron | max ± 0.2 | −0.11 | −0.05 |
| Steel | max ± 0.2 | −0.08 | −0.01 |
| Aluminum | max ± 0.1 | −0.07 | −0.09 |
| Cast iron | max ± 0.2 | −0.06 | ±0.00 |
| Brass | max ± 0.4 | −0.21 | −0.19 |
| Copper | max ± 0.4 | −0.15 | −0.12 |

As compared with the state of the art, the corrosion inhibitor of this invention displays very high protective values, above all in connection with ferrous metals and tin-plated iron. All weight losses, however, correspond to the limit according to DOT 3 as per Federal Motor Vehicle Safety Standard No. 116, S 5.1.6.

EXAMPLE 5

Aqueous, nonflammable hydraulic fluids are utilized nowadays, above all, in hydraulic plants for coal mining in underground operations. The requirements to be met by such fluids are determined in the reports of the Commission of the European Community. In general, the commercial products fulfill many of the posed requirements: good fire resistance, desirable viscosity range with high viscosity index, shear resistance, corrosion-protective power, good low-temperature properties, and criteria meeting mining health care requirements. Protective capacity against wear and tear has remained unsatisfactory thus far.

Such fluids contain at least 40% by weight of water, 32–40% by weight of glycols, and 18–25% by weight of a water-soluble thickener from a mixed adduct of ethylene oxide/propylene oxide in a weight ratio of 3:1 to 1.5:1 with a molecular weight of above 5,000 and inorganic and organic corrosion inhibitors.

A conventional hydraulic fluid based on a polyglycol/water mixture was prepared from the following ingredients:
41% by weight of distilled water
1% by weight of methylmorpholine
0.5% by weight of triethanolamine
0.1% by weight of benzotriazole
37.35% by weight of ethylene glycol
20% by weight of a mixed adduct of ethylene oxide/propylene oxide, molecular weight 12,000
0.05% by weight of a commercial silicone emulsion.

The starting fluid had a viscosity of 38.2 mm²/sec (centistokes) at 50° C., a solidification point of −41° C., a sufficient air release property according to DIN 51 381, and a satisfactory heat stability, satisfying specifications of DIN 51 382.

The following additives were combined with this starting fluid to improve frictional wear protection:
State of the Art (1)
2% by weight of a salt of lauric acid with dibutylamine in a molar ratio of 1:1 (U.S. Patent 2,558,030)
State of the Art (2)
3% by weight of oleic acid triethanolamine salt, likewise in a molar ratio of 1:1 (DAS 1,804,710)
State of the Art (3)
3% by weight of a potassium salt of sebacic acid having a pH value of 7.6 in a 5% aqueous solution (according to U.S. Pat. No. 2,737,497).

State of the Art (4)

0.5% by weight of a diethanolamine salt dodecylsuccinic acid (according to DAS No. 1,594,570)

According to this invention (5)

3% by weight of a diethanolamine salt of isododecyladipic acids

On the four-ball apparatus of Boerlage according to DIN 51 350, one test for each was conducted. The duration was 1 hour with a load of 60 kg. The following spherical wear indentation diameters in mm were determined:

| Starting Fluid | 0.26 | prior art |
| Additive 1 | 0.19 | prior art |
| Additive 2 | 0.18 | prior art |
| Additive 3 | 0.20 | prior art |
| Additive 4 | 0.23 | prior art |
| Additive 5 | 0.14 | according to invention |

Using additive 5 of this invention, a marked improvement was obtained in the frictional wear characteristic. The indicated measured data are averaged values from 6 tests.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. A corrosion inhibited composition comprising
(a) water
(b) a glycol; a polyglycol; a polyglycol ether; a thickener for aqueous compositions; or a mineral oil and an emulsifier; and
(c) an alkali metal salt or a water soluble aliphatic amine salt of a mixture of 2- and 3-$C_{6-12}$-alkyladipic acids, the amount of this acid component being effective as a corrosion inhibitor, and the pH of the composition being 7-9.

2. A corrosion inhibited composition of claim 1 wherein the mixture of alkyladipic acids is prepared by alkylation of phenol, hydrogenation of the alkyl phenol produced, and oxidation of the then produced alkylcyclohexanol to the corresponding alkyladipic acids.

3. A corrosion inhibited composition of claim 1 which is a drilling, cutting or polishing agent wherein the concentration of said corrosion inhibitor is 0.5-3.0% by weight.

4. A corrosion inhibited composition of claim 1 wherein the concentration of said corrosion inhibitor is 1-5% by weight.

5. A corrosion inhibited composition of claim 1 which is an antifreeze composition wherein the concentration of said corrosion inhibitor is 0.6-1.7% by weight.

6. A corrosion inhibited composition of claim 1 which is an antifreeze composition wherein the concentration of said corrosion inhibitor is 0.6-1% and which further comprises a corrosion inhibiting effective amount of another corrosion inhibitor.

7. A composition of claim 1 wherein the corrosion inhibitor is a triethanol- or triisopropanol amine salt of isooctyl-, isononyl-, n-octyl-, n-decyl-, n-dodecyl-, or isododecyladipic acid.

8. A composition of claim 1 wherein the thickener is a water soluble polymer of ethylene oxide and propylene oxide; or a homo- or copolymer of acrylic acid, methacrylic acid or maleic acid or anhydride, and an olefin.

9. A composition of claim 1 wherein the salt is a water soluble aliphatic amine salt.

10. A composition of claim 1 wherein the salt is an alkali metal salt.

11. A method of inhibiting the corrosiveness to metal of an aqueous fluid which comprises adding to the fluid an amount of an alkali metal salt or a water soluble aliphatic amine salt of a mixture of 2- and 3-$C_{6-12}$-alkyladipic acids effective to inhibit corrosion, the pH of the fluid being 7-9.

* * * * *